(12) United States Patent
Niemann et al.

(10) Patent No.: US 12,710,412 B2
(45) Date of Patent: Aug. 18, 2026

(54) SENSOR APPARATUS FOR ANALYZING A SAMPLE GAS VOLUME

(71) Applicant: HELLA GmbH & Co. KGaA, Lippstadt (DE)

(72) Inventors: Thomas Niemann, Delmenhorst (DE); Torsten Eggers, Ganderkesee (DE); Uwe Röben, Zetel (DE); Falko Strackerjan, Bremen (DE)

(73) Assignee: HELLA GmbH & Co. KGaA, Lippstadt (DE)

( * ) Notice: Subject to any disclaimer, the term of this patent is extended or adjusted under 35 U.S.C. 154(b) by 325 days.

(21) Appl. No.: 18/542,117

(22) Filed: Dec. 15, 2023

(65) Prior Publication Data

US 2024/0201154 A1 Jun. 20, 2024

(30) Foreign Application Priority Data

Dec. 16, 2022 (DE) ..................... 10 2022 133 636.0

(51) Int. Cl.
*G01N 1/28* (2006.01)
*G01N 33/00* (2006.01)

(52) U.S. Cl.
CPC ........... *G01N 33/0047* (2013.01); *G01N 1/28* (2013.01); *G01N 33/0073* (2013.01)

(58) Field of Classification Search
CPC ... G01N 1/28; G01N 33/0047; G01N 33/0073
See application file for complete search history.

(56) References Cited

U.S. PATENT DOCUMENTS

2007/0229825 A1* 10/2007 Bates ................. G01N 15/1459 356/339
2017/0177009 A1* 6/2017 Neander ................ G01N 15/14
2018/0356383 A1* 12/2018 Phelipot ............. G01N 33/0075
2020/0011779 A1* 1/2020 Lavrovsky ............. G01N 15/06

FOREIGN PATENT DOCUMENTS

DE 102019103885 A1 * 8/2020 ............. G01N 21/53

* cited by examiner

*Primary Examiner* — Jamel E Williams
(74) *Attorney, Agent, or Firm* — MUNCY, GEISSLER, OLDS & LOWE, P.C.

(57) ABSTRACT

A sensor apparatus for analysing a sample gas volume includes at least one fine particle measuring chamber to hold the sample gas that is to be analysed, at least one sensor element for measuring fine particles assigned to the fine particle measuring chamber, at least one sample gas feed assigned to the fine particle measuring chamber, at least one sample gas discharge assigned to the fine particle measuring chamber, at least one ventilation device assigned to the fine particle measuring chamber. The ventilation device includes a fan with a fan housing, and the sensor apparatus has at least one circuit carrier with at least one control circuit for actuating the ventilation device. The circuit carrier incudes a circuit for controlling the measurement of fine particles. The circuit carrier is arranged outside the fan housing. The ventilation device has a data interface for a data-carrying connection to the circuit carrier.

8 Claims, 2 Drawing Sheets

SENSOR APPARATUS FOR ANALYZING A SAMPLE GAS VOLUME

BACKGROUND OF THE INVENTION

Field of the Invention

The invention relates to a sensor apparatus for analysing a sample gas volume, in particular for measuring fine particles in a sample gas volume, with at least one fine particle measuring chamber to accommodate the sample gas that is to be analysed, wherein at least one sensor element for measuring fine particles is assigned to the fine particle measuring chamber, with at least one sample gas feed assigned to the fine particle measuring chamber, with at least one sample gas discharge assigned to the fine particle measuring chamber, with at least one ventilation device assigned to the fine particle measuring chamber, wherein the ventilation device includes a fan with a fan housing, and wherein the sensor apparatus has at least one circuit carrier with at least one control circuit for actuating the ventilation device. A further aspect of the invention relates to a ventilation device for a sensor apparatus for capturing the fine particle content of a sample gas volume, wherein the ventilation device includes a fan and a fan housing.

Description of the Related Art

Measuring devices for measuring fine particles are used in a wide range of motor vehicles. For example, a measuring device of such kind may be used to test the air around the motor vehicle for the presence of fine dust particles. In this application, optical measurement procedures may be employed, in which an air volume to be analysed is irradiated in a measuring chamber by a laser, and the change in the laser beam is captured by means of an optical receiver device. For this purpose, a measuring chamber may be provided in which the sample gas volume to be tested is analysed. A sample gas feed and a sample gas discharge may be connected to the measuring chamber for this purpose. A ventilation device with a fan and a fan housing is provided in order to transport the sample gas volume, that is to say create a sample gas flow.

A disadvantage of known sensor apparatuses is that further measurements must be integrated in such a sensor apparatus in order to determine further parameters of the sample gas volume, for example the humidity, temperature or air quality, all of which are necessarily associated with substantial expense. It is not possible to integrate these functions in a basic fine particle sensor subsequently without significant expense because of installation space limitations and the gas flow management which is strictly defined thereby.

BRIEF SUMMARY OF THE INVENTION

The problem addressed by the invention is to suggest a sensor apparatus for analysing a sample gas volume with which it is possible to expand the function to include recording further parameters.

This problem is solved with a sensor apparatus having the features of claim 1 and with a ventilation device having the features of claim 7.

In a sensor apparatus for analysing a sample gas volume, in particular for measuring fine particles in a sample gas volume, with at least one fine particle measuring chamber for holding the sample gas to be analysed, wherein at least one sensor element for measuring fine particles is assigned to the fine particle measuring chamber, with at least one sample gas feed assigned to the fine particle measuring chamber, with at least one sample gas discharge assigned to the fine particle measuring chamber, with at least one ventilation device assigned to the fine particle measuring chamber, wherein the ventilation device has a fan with a fan housing, and wherein the sensor apparatus has at least one circuit carrier with at least one control circuit for actuating the ventilation device, it is provided as essential to the invention that the circuit carrier has a circuit for controlling the measurement of fine particles, that the circuit carrier is arrange outside the fan housing, and that the ventilation device has at least one data interface for data-carrying connection to the circuit carrier. The sample gas may be for example the air in the passenger compartment and/or the air surrounding a vehicle. The sensor apparatus may be arranged inside a motor vehicle, for example. The sensor apparatus for analysing a sample gas volume, in particular for measuring fine particles, includes a circuit carrier, wherein a circuit both for controlling the measurement of fine particles, that is to say the sensor elements in the fine particle measuring chamber, and for controlling the fan of the ventilation device, is arranged on said circuit carrier. For this purpose, the ventilation device is equipped with a data interface for data-carrying connection to the controller of the circuit carrier. The circuit carrier is arranged outside the fan housing. In particular, the sensor apparatus may include a sensor housing, in which the fan housing and the circuit carrier are arranged. By relocating the circuit carrier from the interior of the fan housing to outside the fan housing, it is possible to create additional installation space inside the fan housing, which is then available for other purposes. Moreover, this also means that the circuit carrier has no contact with the stream of the sample gas, so that no apparatuses are needed to protect the circuit carrier, such as an encapsulation or coating to protect the circuit carrier from the environmental influences of the gas flow. Thus, the installation space in the fan housing made available in this way may accommodate further sensor elements, which can be used to measure more parameters of the sample gas volume, such as the relative humidity, temperature, or quality of the air. The circuit for controlling the additional measurements may be arranged on the circuit carrier outside the fan housing, on which the control circuit for the fan device is also arranged. In this way, further measurement methods may be added to the sensor apparatus without needing additional installation space for the sensor apparatus. It is also possible for a desired feature of the sensor apparatus to be adapted at the factory by choosing differently equipped ventilation devices for different application cases, wherein the ventilation devices are equipped with corresponding sensor elements. The necessary circuits, which can be actuated correspondingly, may be arranged on the one circuit carrier.

In a further development of the invention, the fan housing has at least one sensor element for capturing at least one further parameter of the sample gas to be analysed, and at least one control circuit for controlling the capture of the at least one further parameter of the sample gas to be analysed is arranged on the circuit carrier. A sensor element for capturing a further parameter may be for example a humidity sensor, a flow sensor, an air quality sensor, a sensor for detecting volatile organic substances, a temperature sensor, or the like. The corresponding sensor elements are arranged inside the fan housing, wherein a measuring chamber may be created in the fan housing for analysing the sample gas stream. The circuit carrier, which is arranged outside the fan housing, may include corresponding circuits that are designed to control the corresponding parameter measurements. In this way, an extension of the measuring capability of the sensor apparatus by exchanging the fan housing is enabled without affecting the installation space for the sensor apparatus or the need to install a new circuit carrier.

In a further development of the invention, the circuit carrier has no contact with the sample gas volume to be analysed. Since the circuit carrier is arranged outside the fan housing and outside the lines that carry the sample gas, such as the sample gas feed and the sample gas discharge, the circuit carrier does not come into contact with the sample gas volume that is to be analysed. An encapsulation, coating, or other protective means for the circuit carrier to shield it from the effects of the sample gas are therefore unnecessary.

In a further development of the invention, the sensor apparatus has at least one further measuring chamber for capturing the at least one further parameter of the sample gas volume to be analysed, and the further measuring chamber is arranged inside the fan housing. The fan housing includes a measuring chamber for the purpose of measuring further parameters of the sample gas volume that is to be analysed. In particular, the measuring chamber for the further parameters may be arranged in the installation space inside the fan housing, in which actually a circuit carrier is provided for controlling the fan. The circuit for the fan is arranged on the circuit carrier outside the fan housing, inside the sensor housing. With the additional measuring chamber, which is arranged inside the fan housing, it is possible to take precise measurements of further parameters of the sample gas volume without the need for a larger installation space for the sensor apparatus.

In a further development of the invention, the fan housing is selectable according to the application case of the parameters to be determined, and the fan housing is adapted for capturing the respective further parameters to be detected. The fan housing may contain sensor elements for determining the further parameters. For this purpose, the fan housing may also include a measuring chamber, in which the sample gas volume is analysed. The fan housing may be adapted to an application case as desired by the arrangement of the sensor elements and the measuring chamber. Thus, for example, a correspondingly adapted fan housing may be installed in a vehicle in which it should be possible to take measurements of temperature, flow rate and fine particles, without needing to modify other devices of the sensor apparatus. For example, the circuit carrier with the control circuits may remain unchanged for this. Each of the circuits that are needed for the respective analysis methods may be used.

In one embodiment of the invention, one of the further parameters to be captured of the sample gas volume to be analysed is the humidity and/or the temperature of the air and/or the presence of harmful gases and/or the presence of volatile organic compounds. The fan housing may be equipped with sensor devices for capturing such parameters. For example, the fan housing may also include a sensor for measuring the volume flow rate.

A further aspect of the invention relates to a ventilation device for a sensor apparatus for capturing at least the fine particle content of a sample gas volume, wherein the ventilation device includes a fan and a fan housing, wherein it is provided as essential to the invention that the ventilation device has at least one data interface for a data-carrying connection with a circuit carrier arranged outside the fan housing, wherein the circuit carrier contains at least one control circuit for actuating the ventilation device and for controlling at least one measurement of a parameter of the sample gas volume. A circuit carrier that is arranged outside the fan housing, in particular arranged inside the sensor housing of the sensor apparatus, is assigned to the ventilation device. The arrangement of the control circuit outside the fan housing has the effect of creating additional space in the fan housing, in which further sensor elements can be arranged for measuring additional parameters. Another consequence of arranging the circuit carrier outside the fan housing is that the circuit carrier is prevented from coming into contact with the air volume that is to be analysed, so that protective apparatuses for shielding the circuit carrier from external influences can be dispensed with.

In a further development of the invention, the fan housing includes at least one sensor element for capturing at least one further parameter of the sample gas volume to be analysed. A sensor element for capturing a further parameter may be for example a humidity sensor, a flow sensor, an air quality sensor, a sensor for detecting volatile organic substances, a temperature sensor, or the like. The sensor elements are arranged inside the fan housing, wherein a measuring chamber may be created inside the fan housing for analysing the sample gas stream here. The circuit carrier, which is arranged outside the fan housing, may include corresponding circuits which are designed to control the corresponding parameter measurements. In this way, an expansion of the measuring capability of the sensor apparatus is made possible by replacing the fan housing, without affecting the installation space of the sensor apparatus or having to provide a new circuit carrier.

In a further development of the invention, the fan housing includes at least one measuring chamber for capturing the at least one further parameter of the sample gas volume to be analysed. The fan housing has a measuring chamber for measuring further parameters of the sample gas volume to be analysed. In particular, the measuring chamber for the further parameters may be arranged in the installation space inside the fan housing, in which actually a circuit carrier is provided for controlling the fan. The circuit for the fan is arranged on the circuit carrier outside the fan housing, inside the sensor housing. With the additional measuring chamber, which is arranged inside the fan housing, it is possible to take precise measurements of further parameters of the sample gas volume without the need for a larger installation space for the sensor apparatus.

In a further development of the invention, the sensor element is designed to capture at least one further parameter for detecting the humidity and/or the temperature of the air and/or the presence of harmful gases and/or the presence of volatile organic compounds. The fan housing may be equipped with sensor devices for capturing such parameters. For example, the fan housing may also include a sensor for measuring the flow rate.

BRIEF DESCRIPTION OF DRAWINGS

In the following text, the invention will be explained in greater detail with reference to the exemplary embodiment represented in the drawing. In detail, the schematic representations in the drawing show, in.

DETAILED DESCRIPTION OF THE INVENTION

Figure 1:
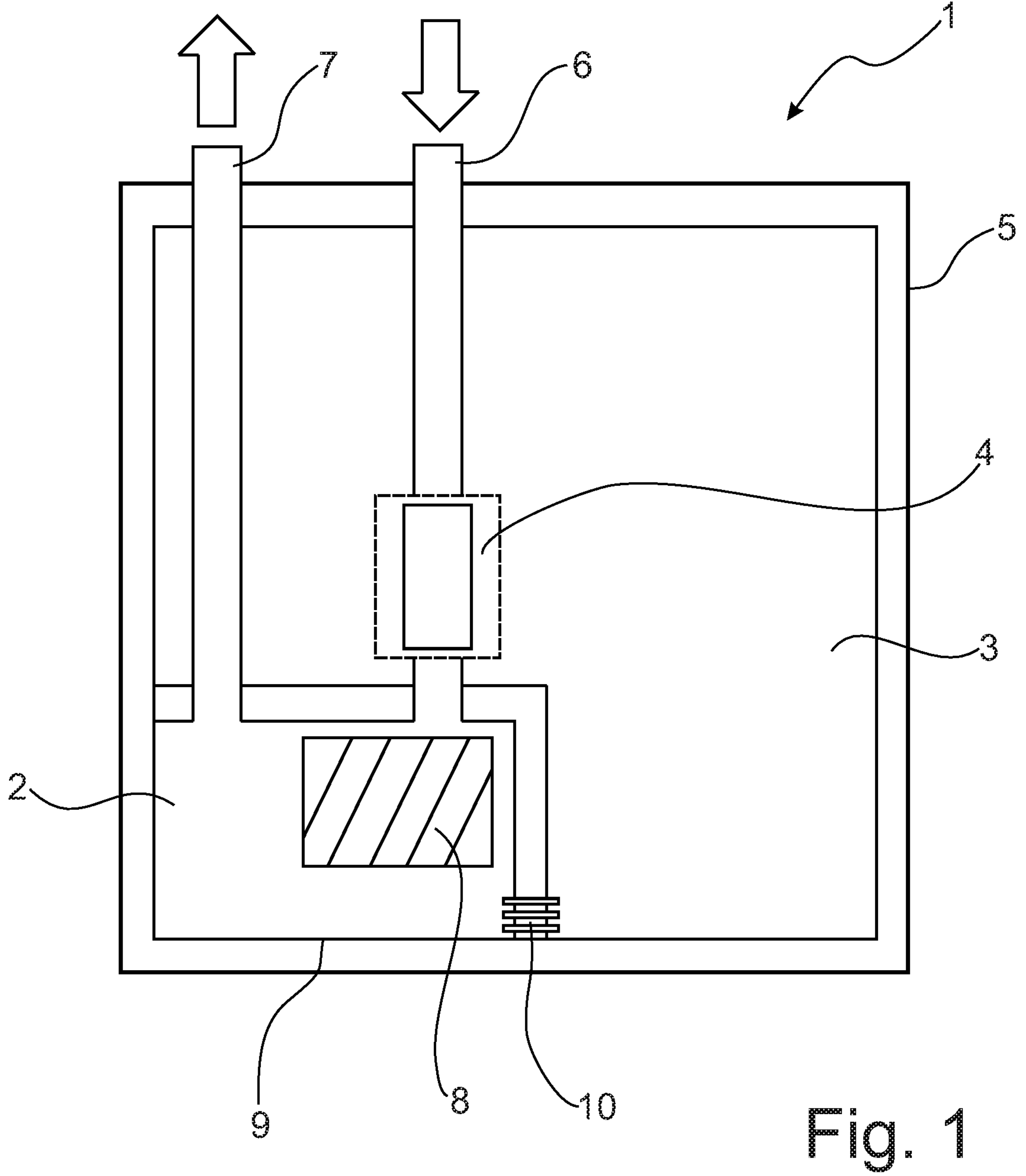
FIG. 1: a sensor apparatus for measuring fine particles, with a ventilation device, a circuit carrier and a fine particle measuring chamber.

FIG. 1 is a schematic representation of a sensor apparatus 1 with a ventilation device 2, a circuit carrier 3 and a fine particle measuring chamber 4. The sensor apparatus 1 includes a sensor housing 5, in which the circuit carrier 3 as well as the ventilation device 2 and the fine particle measuring chamber 4 are arranged. The sensor apparatus 1 has a sample gas feed 6 and a sample gas discharge 7, through which the sample gas is fed into the fine particle measuring chamber 4 and transported out of it again. In order to create the gas stream, the ventilation device 2 has a fan 8 inside a fan housing 9. At least one control circuit for the ventilation device 2 and one control circuit for the fine particle measurement are arranged on the circuit carrier 3. The ventilation device 2 is connected in a manner that allows data to be carried to the circuit carrier 3 and thus also to the control circuit arranged on the circuit carrier 3 via a data interface 10.

Figure 2:
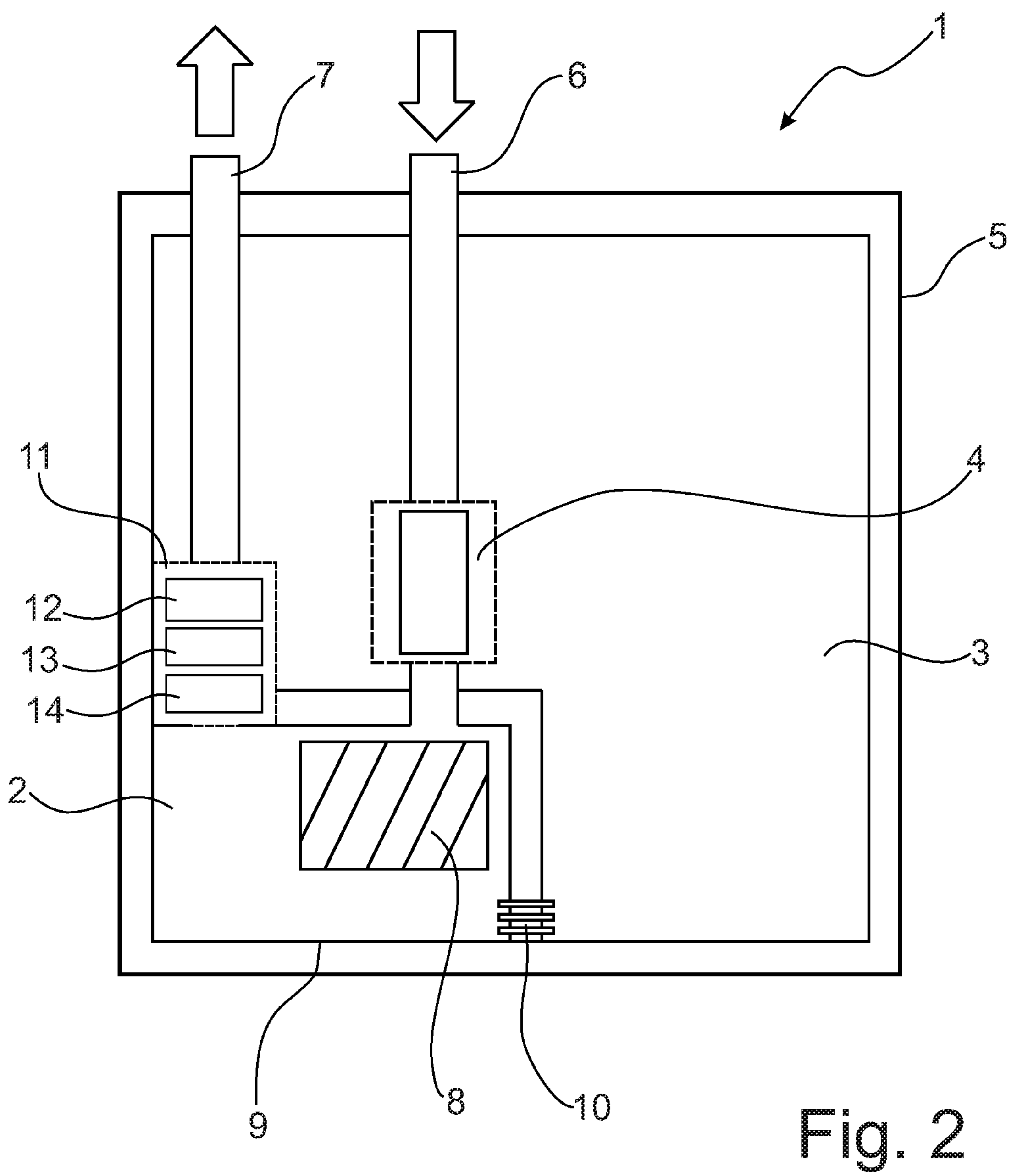
FIG. 2: a sensor apparatus according to FIG. 1 with additional measurement functions.

FIG. 2 represents a sensor apparatus 1 according to FIG. 1 with additional measurement functions. Identical components are denoted with the same reference numerals. Since the circuit carrier 3 with the control circuit is not arranged inside the fan housing 9 but instead on the circuit carrier 3 inside the sensor housing 5, additional installation space is created inside the fan housing 9. A further measuring chamber 11 may be arranged therein. Additional sensor elements, such as a temperature sensor 12, a humidity sensor 13 and an air quality sensor 14 may be assigned to the measuring chamber 11. Since the measuring chamber 11 with the sensor elements 12-14 is arranged inside the fan housing 9, it is possible to adapt a sensor apparatus 1 for a desired application. For example, if a vehicle is to be constructed that measures the temperature and humidity in a sample gas volume, a correspondingly designed ventilation device 2 may be installed in the sensor housing 5. The corresponding control circuits, for measuring the temperature and humidity of the air, and/or measuring air quality, for example, may be provided on the circuit carrier 3 and actuated depending on requirements.

The invention claimed is:

1. A sensor apparatus for analysing a sample gas volume, in particular for measuring fine particles in a sample gas volume, with at least one fine particle measuring chamber to accommodate the sample gas that is to be analysed, wherein at least one sensor element for measuring fine particles is assigned to the fine particle measuring chamber, with at least one sample gas feed assigned to the fine particle measuring chamber, with at least one sample gas discharge assigned to the fine particle measuring chamber, with at least one ventilation device assigned to the fine particle measuring chamber, wherein die ventilation device includes a fan with a fan housing, and wherein the sensor apparatus has at least one circuit carrier with at least one control circuit for actuating the ventilation device, wherein the circuit carrier has a circuit for controlling the measurement of fine particles, the circuit carrier is arranged outside the fan housing, and the ventilation device has at least one data interface that allows a data-carrying connection to the circuit carrier, wherein the fan housing has at least one sensor element for capturing at least one further parameter of the sample gas volume to be analysed, and that at least one control circuit is arranged on the circuit carrier for controlling the capture of the at least one further parameters of the sample gas volume to be analysed.

2. The sensor apparatus according to claim 1, wherein the circuit carrier has no contact with the sample gas volume that is to be analysed.

3. The sensor apparatus according to claim 1, wherein the sensor apparatus includes at least one further measuring chamber for capturing the at least one further parameter of the sample gas volume to be analysed, and that the further measuring chamber is arranged inside the fan housing.

4. The sensor apparatus according to claim 1, wherein the fan housing is selectable depending on the application case of the parameters to be captured, and that the fan housing is adapted for capturing the respective further parameters that are to be determined.

5. The sensor apparatus according to claim 1, wherein one of the further parameters to be captured of the sample gas volume to be analysed is the humidity and/or the temperature of the air, and/or the presence of harmful gases and/or the presence of volatile organic compounds.

6. A ventilation device for a sensor apparatus for detecting at least the fine particle content of a sample gas volume, wherein the ventilation device includes a fan and a fan housing, wherein the ventilation device has at least one data interface to allow a data-carrying connection to a circuit carrier arranged outside the fan housing, wherein the circuit carrier includes at least one control circuit for actuating the ventilation device and for controlling at least one measurement of a parameter of the sample gas volume, wherein the fan housing has at least one sensor element for capturing at least one further parameter of the sample gas volume to be analysed.

7. The ventilation device according to claim 1, wherein the fan housing contains at least one measuring chamber for capturing the at least one further parameter of the sample gas volume to be analysed.

8. The ventilation device according to claim 6, wherein at least one sensor element is designed to capture at least one further parameter for detecting the humidity and/or the temperature of the air and/or the presence of harmful gases and/or the presence of volatile organic compounds.

* * * * *